United States Patent [19]

Libs

[11] 3,972,004

[45] July 27, 1976

[54] CHARGE PREAMPLIFIER

[75] Inventor: Gérard Libs, Gif-sur-Yvette, France

[73] Assignee: Commissariat a l'Energie Atomique, Paris, France

[22] Filed: Nov. 26, 1974

[21] Appl. No.: 527,201

[30] Foreign Application Priority Data

Nov. 27, 1973  France .............................. 73.42158

[52] U.S. Cl. .............................. 330/35; 307/235 T; 307/296; 330/18; 330/23; 330/26; 330/59
[51] Int. Cl.[2] .......................................... H03F 3/16
[58] Field of Search .................. 330/18, 23, 26, 35, 330/59; 307/235 T, 296

[56] References Cited
UNITED STATES PATENTS 3,286,189  11/1966  Mitchell et al. .................... 330/35 X
3,611,173  10/1971  Goulding et al. ..................... 330/59

OTHER PUBLICATIONS

Landis et al. — "Pulsed Feedback Techniques for Semi-Conductor Detector Radiation Spectrometers" *IEEE Transactions on Nuclear Science* pp. 115–124, vol. NS-18, No. 1, Feb. 1971.
Kurz — "Low-Noise Preamplifier for High Count Rates" *IEEE Transactions on Nuclear Science*, pp. 418–422, vol. NS-49, No. 3, June, 1972.
McQuaid — "A High-Rate Direct Coupled Preamplifier for High Energy Ge Detector Systems," *IEEE Transactions on Nuclear Science*, pp. 396–402, vol. NS-19, No. 1, Feb. 1972.
Libs — "Highresolving Power Load Preamplifier" *l'Onde Electronique* (France), pp. 1368–1371, vol. 47, No. 488 bis, Nov. 1967.

*Primary Examiner*—R. V. Rolinec
*Assistant Examiner*—Lawrence J. Dahl
*Attorney, Agent, or Firm*—Lane, Aitken, Dunner & Ziems

[57] ABSTRACT

The charge preamplifier comprises an input stage driven by the signal to be amplified, the input stage being connected to an amplification stage associated with an output stage, and a circuit for applying opto-electronic feedback from the output to the input of the preamplifier. The input stage comprises a cooled field-effect transistor, the signal to be amplified being applied to the input gate of the transistor. The load resistance of the transistor is provided by a second field-effect transistor mounted in series with an inductance coil.

5 Claims, 4 Drawing Figures

CHARGE PREAMPLIFIER

This invention relates to a charge preamplifier.

It is known that semiconductor detectors of the lithium-compensated silicon type are advantageously employed in the fluorescence analysis of light elements and therefore in the detection of low-energy X-rays. The detector is associated with a measuring system which is intended to measure the number of counts as a function of energy, tht is to say the number of pulses delivered by said detector, each pulse being intended to correspond to the arrival of a particle. The measuring system must clearly have a very high resolving power which in fact depends on the quality and dimensions of the detector as well as the associated electronic circuit and in particular on the charge preamplifier which is placed at the head of this electronic circuit. In general, efforts have consequently been directed to the reduction of noise of the components which constitute the input stage of the preamplifier. In order to reduce this noise, a certain number of devices have already been constructed.

The prior art can be illustrated by the preamplification device described in the review entitled "Nuclear Instrument and Methods," 71, 1969, pages 273 to 279. In this device, the input of the preamplifier is constituted by a field-effect transistor which will be designated hereinafter as a FET, said transistor being placed within a cryostat in the vicinity of the detector, thus reducing its noise as well as stray capacitances. Moreover, a new feedback technique in the so-called optoelectronic field has been adopted for the preamplifier and permits a very appreciable improvement in the resolving power irrespective of the count rate. The feedback resistor is replaced by an electroluminescent diode which is intended to shine on the input FET. The noise contribution from the feedback element is much lower in this case. However, further high noise sources also exist and are primarily due to the nature of the resistance of the load on the input FET.

A clearer understanding of this problem will be gained by referring to the accompanying FIG. 1 in which the input stage of a preamplifier in accordance with the prior art is shown diagrammatically.

In this figure, the signal delivered by the detector is applied to the input gate G of the field-effect transistor T' which is cooled. The source input of the transistor is connected to ground whilst its drain input is connected to the emitter of the bipolar transistor T. The common point of the two transistors is connected to the supply line 2 through the emitter resistor $R_1$. The collector of the transistor T is connected to the second supply line through the collector resistor $R_2$. The output of the input stage of the preamplifier is located at point A. The noise sources which disturb the measurements have different origins. These noises are given by the following formulae:

$\overline{i_0}^2$ represents the intensity of the noise produced by the channel current of the transistor T', $\overline{i_b}^2 = 2qI_b$ represents the partition noise produced within the transistor T.

The resistors $R_1$ and $R_2$ produce not-negligible levels of noise, $\overline{i_1}^2 = (4KT/R_1)$ represents the intensity of the noise produced by the resistor $R_1$.

$\overline{i_2}^2 = (4KT/R_2)$ represents the intensity of the noise produced by the resistor $R_2$.

In these formulae, $q$ is the elementary charge, $K$ is the Boltzman constant and $T$ is the absolute ambient temperature.

It is noted on the one hand that the values of the resistors $R_1$ and $R_2$ must be high in order to reduce the levels of noise $\overline{i_1}^2$ and $\overline{i_2}^2$ and on the other hand that the transistor T must be selected from those which have a very high current gain in order to reduce the noise $\overline{i_b}^2$. The first of these observations presupposes a high value of the input voltage which is not always possible in practice. Moreover, it is recommended practice to employ a FET instead of the bipolar transistor T when the drive is applied through a high resistance as in this instance. The n-type transistor could be replaced only by a p-type FET. Unfortunately, the noise level of this latter is much too high compared with an n-type transistor and even with a bipolar transistor.

This invention is precisely directed to a charge preamplifier which overcomes th disadvantages mentioned in the foregoing by suppressing or at least considerably reducing the noise produced by the input stage of the preamplifier.

The charge preamplifier essentially comprises an input stage driven by the signal to be amplified, said stage being connected to an amplification stage which is in turn associated with an output stage, and a circuit for applying feedback from the output to the input of said preamplifier, said feedback being of the optoelectronic type, said input stage being such as to comprise a cooled field-effect transistor, the signal to be amplified being applied to the input gate of said transistor, the load resistance of said transistor being provided by a second field-effect transistor mounted in series with an inductance coil.

In accordance with a first characteristic feature of the invention, the impedance of said inductance coil within the frequency range of the preamplifier is considerably higher than the reciprocal of the slope of the field-effect load transistor.

In accordance with a second characteristic feature, the drain output of the input transistor is connected on the one hand to the source input of the load transistor through said inductance coil which is mounted in series with a resistor and on the other hand to the input gate of said load transistor.

In accordance with a third characteristic feature, the input stage is followed by a differential stage comprising a field-effect transistor and a bipolar transistor.

In accordance with a further characteristic feature, the feedback circuit comprises a hysteresis comparator having one input connected to the output of the preamplifier output stage and the other output connected to a reference voltage source, the output of said comparator being connected to a device for initiating the supply of an electroluminescent diode placed opposite to the input transistor through a capacitor in which one plate is connected to the output of the preamplifier output stage and the other plate is connected to the input gate of the input field-effect transistor.

A more complete understanding of the invention will in any case be obtained from the following description of one embodiment which is given by way of example but not in any limiting sense, reference being made to the accompanying drawings, in which:

FIG. 1 as hereinabove described is a diagram of the input stage of a preamplifier in accordance with the prior art;

Figure 1:
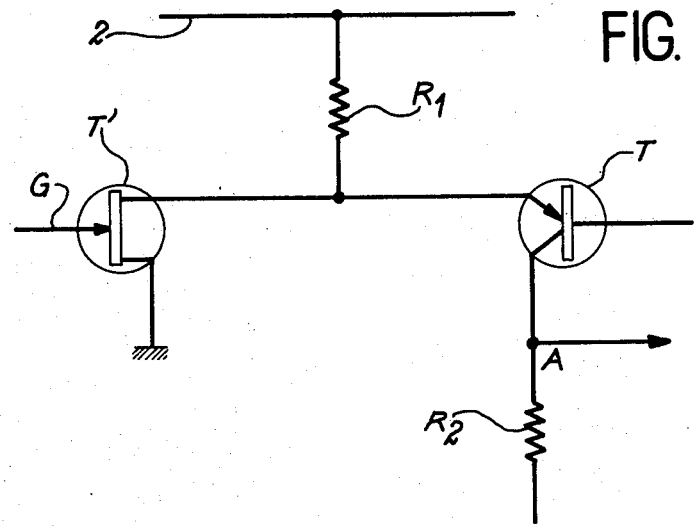
Figure 2:
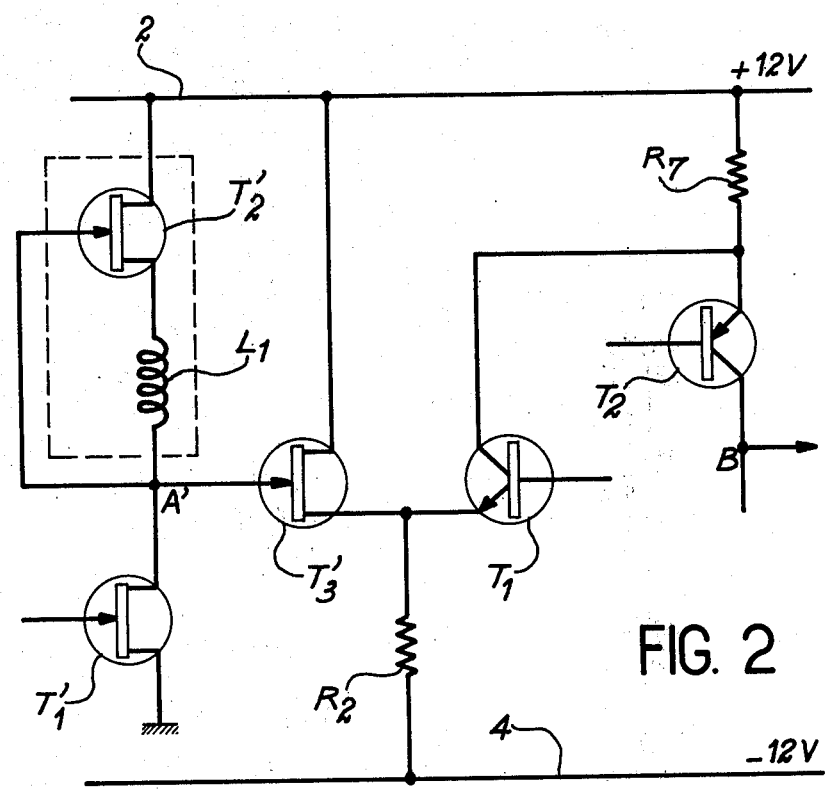
FIG. 2 is a diagram of the input stage of the preamplifier in accordance with the invention.

The input of the preamplifier in accordance with the invention is shown in detail in FIG. 2. There can be seen in this figure the FET $T'_1$, the input gate of which is driven by the signal delivered by the detector. The source input of the FET $T'_1$ is connected to ground whilst the drain of said FET is connected on the one hand to the source input of the load FET $T'_2$ through the inductance coil $L_1$ and on the other hand to the gate of the FET $T'_2$. The drain of the FET $T'_2$ is connected to the line 4 for supplying voltage at +12 volts. The drain of the FET $T'_1$ (at the point A) is connected to the gate of the FET $T'_3$ which constitutes a differential circuit in conjunction with the bipolar transistor $T_1$. The source of the FET $T'_3$ and the emitter of the transistor $T_1$ are connected to the −12 volt supply line 4 through the bias resistor $R_2$. The values of the supply voltages are obviously given only by way of example and correspond to types of components which are the most widely employed. The bipolar transistor $T_2$ constitutes a parallel cascode circuit in conjunction with the transistor $T_1$. The collector of the transistor $T_1$ and the emitter of the transistor $T_2$ are connected to the line 2 through the resistor $R_7$. The three transistors $T'_3$, $T_1$ and $T_2$ constitute the second amplification stage of the preamplifier. The collector output (point B) of the transistor $T_2$ is connected to the output stage of the preamplifier.

In this circuit arrangement, the transistor $T'_1$ is provided with a load resistance by the field-effect transistor $T'_2$. Gain degeneration of the FET $T'_2$ is caused by the presence of the inductance coil $L_1$ in order to reduce as far as possible the variations of the current which passes through said FET. The noise intensity $i^2$ at the point A' is then obtained substantially as follows:

$$\overline{i^2} = \overline{i_{D1}^2} + \overline{i_{D2}^2} \left(\frac{1/S_2}{L_1\omega}\right)^2$$

wherein $\overline{i_{D1}^2}$ and $\overline{i_{D2}^2}$ represent respectively the noise produced by the channel current of the FETs $T'_1$ and $T'_2$. In this formula, $S_2$ is the slope of the FET $T'_2$. It is clearly necessary to ensure that the impedance $L_1\omega$ is substantially higher than the term $1/S_2$ within the frequency range employed by the filter of the amplifier. The value adopted for the inductance coil $L_1$ is approximately 200 to 300 mH, this value being determined experimentally by establishing that the noise level measured by the quadratic voltmeter at the output of the amplification circuit becomes practically insensitive to the type of transistor which is chosen as a load device. In the case of the transistor $T'_2$, it is preferable to employ a transistor of type 2N 4416 (Texas) and the same applies to the transistor $T'_1$.

The FET $T'_3$ is selected from those which have a high slope although the value of current $I_D$SS must nevertheless not be too high, $I_D$SS being the value of the drain current in respect of a zero gate-source bias. The transistor $T_1$ which is the second element of the differential stage is preferably a bipolar transistor having a current gain $\omega$ which is at least equal to 200. In this circuit arrangement, there remains only one noise generator represented by the noise intensity of the transistor $T'_1$ since the noise of the transistor $T'_2$ can be considered as negligible. The Miller effect produced by this arrangement has practically no effect on the signal-to-noise ratio of the amplifier.

Figure 3:
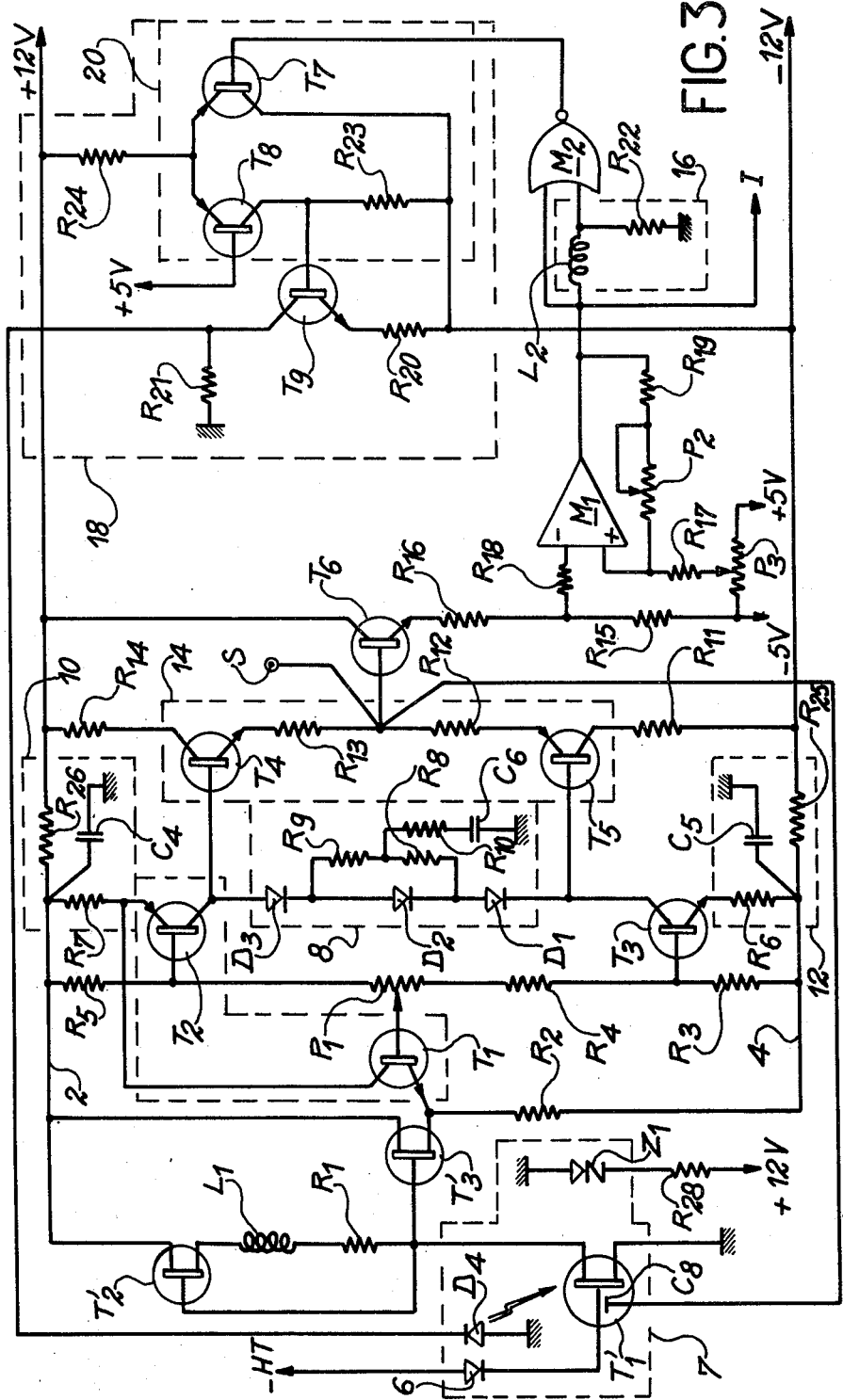
FIG. 3 is a circuit diagram of the complete preamplifier in accordance with the invention.

There is shown in FIG. 3 one example of construction of the preamplifier in accordance with the invention and comprising the input stage which has already been described with reference to FIG. 2. This figure shows the detector 6 (which is for example of the lithium-compensated silicon type) supplied by a voltage source −HT through a filter if necessary. The detector 6 and the FET $T'_1$ are placed within a cryostat as shown by the dashed outline 7 and maintained at a very low temperature. The load resistance of the transistor $T'_1$ comprises in addition to the transistor $T'_2$ and the inductance coil $L_1$ a resistor $R_1$ which is mounted in series with said inductance coil.

The amplification stage proper of the preamplifier further comprises the bipolar transistors $T_1$ and $T_2$, a filter network 8 and a load transistor $T_3$. The filter network 8 comprises in known manner the resistors $R_8$, $R_9$, $R_{10}$ and the capacitor $C_6$. The filter circuit 8 is connected to the transistor $T_2$ through the diode $D_3$ and to the collector of the load transistor $T_3$ through the diode $D_1$. The filter circuit 8 which is a low-pass filter is intended to correct the frequency response of the preamplifier. There are also shown in the figure the different transistor bias resistors, namely the resistors $R_6$ and $R_3$ for the transistor $T_3$, the resistor $R_4$, the resistor $R_5$ and the potentiometer $P_1$ for the transistor $T_1$, the resistor $R_5$ for the base of the transistor $T_2$. Moreover, the supply lines 2 and 4 for the amplification stage and the input stage are connected to the voltage sources through two coupling cells 10 and 12 respectively which are constituted respectively by the resistor $R_{26}$ and the capacitor $C_4$, and by the resistor $R_{25}$ and the capacitor $C_5$.

The output stage 14 of the preamplifier is essentially constituted by the bipolar transistors $T_4$ and $T_5$, the bases of which are connected respectively to the collectors of the transistors $T_2$ and $T_3$. There are also shown the protective resistors $R_{11}$ and $R_{14}$ of these transistors and the emitter resistors $R_{12}$ and $R_{13}$ in which the point of connection constitutes at the same time the output S of the preamplifier.

The preamplifier further comprises a feedback system of the optoelectronic type. This system comprises a bipolar transistor $T_6$, the base of which is connected to the point of output S of the preamplifier and the emitter of which is connected to the reverse input of a hysteresis comparator $M_1$ through a voltage divider which also serves to bias said transistor $T_6$ and is constituted by the resistors $R_{16}$ and $R_{15}$. The forward input of the comparator is connected to a reference voltage source constituted by the potentiometer $P_3$ which is supplied between the voltages of −5 volt, +5 volts, and by the resistor $R_{17}$. The comparator $M_1$ comprises a feedback circuit constituted by the resistor $R_{19}$ and the potentiometer $P_2$. The potentiometer $P_3$ makes it possible to adjust the centering of the comparator $M_1$ whilst the potentiometer $P_2$ serves to adjust the dynamic output characteristics of the preamplifier. The (logical) output of the comparator $M_1$ is connected to the input of the logical gate $M_2$. The second input of the logical gate $M_2$ is also connected to the output of the comparator $M_1$ through an integrating circuit 16 constituted in known manner by the inductance coil $L_2$ and by the resistor $R_{22}$. This integrating circuit serves to introduce a time-delay in the logical signal delivered by the comparator $M_1$. The output of the logical gate $M_2$ which is advantageously constituted by a NOR gate drives a circuit 18 for controlling an electroluminescent diode $D_4$ placed within the cryostat 7 opposite to the FET $T'_1$. The emitter output of the transistor $T_9$ is preferably connected to the supply line 4 through the resistor $R_{20}$. The transistor collector $T_9$ comprises the resistor $R_{21}$ and the base of the transistor $T_8$ is connected to a voltage supply of +5 volts. The transistor $T_7$ which is associated with the transistor $T_8$ constitutes the bistable device 20.

The output S of the preamplifier is also connected to a feedback capacitor $C_8$ placed between the detector 8 and the FET $T'_1$. There is also placed within the cryostat 7 a Zener diode $Z_1$, one terminal of which is connected to a voltage supply of +12 volts through the resistor $R_{28}$.

The operation of the preamplifier is as follows. When the action of the charges stored in the detector is such that the voltage delivered by the preamplifier at its output S is higher than the threshold value preset by means of the potentiometers $P_2$ and $P_3$, the hysteresis comparator circuit $M_1$ delivers the logical signal O. At the end of the period $t$ corresponding to the time-delay introduced by the integrating circuit 16, two signals of logical level O appear at the inputs of the logical gate $M_2$ which is constituted by a NOR circuit. Said gate therefore delivers a signal of logical level 1 which initiates the transition of the circuit 20. This reversal of state triggers the transistor $T_9$ into conduction and this latter therefore supplies the electroluminescent diode $T_4$. Said diode shines on the gate-drain junction of the FET $T'_1$. The resultant increase in the reverse current within said junction causes the feedback capacitor $C_8$ to discharge for a period of time which depends on the current within the transistor $T_9$ and therefore on the value of the resistor $R_{20}$. When the output voltage of the preamplifier attains the bottom threshold value determined by the hysteresis comparator $M_1$, the bistable circuit 20 returns to its initial state, with the result that the current within the diode $D_4$ is cut-off. The output I of the comparator $M_1$ constitutes an inhibition output for the device which serves to record the output voltage S of the preamplifier.

The drain voltage of the FET $T_1$ can be adjusted by means of the potentiometer $P_1$ to a value of the order of 5 volts. Depending on the transistor which is employed, it is usually necessary to set this value between 4 and 5 volts so as to obtain the best resolution. The resistor $R_1$ makes it possible to control the drain current of the transistor $T'_1$ independently of its drain voltage. A value of 500 ohms is preferably employed for the resistor $R_1$ in the case in which the input FETs are of the type designated as 2N 4416 (Texas). The potentiometers $P_2$ and $P_3$ make it possible to adjust the dynamic output characteristics within a range which, in the example described, has a maximum value of +1.5 volts and a minimum value of −1.5 volts.

Under these conditions, in the case of count rates of 4300 counts per second and 130,000 counts per second, the reset period is respectively equal to 186 ms and 4.4 ms in the case of a Fe-55 source (of the order of 6 keV energy). The time of return of the preamplifier is adjustable by means of the resistor $R_{20}$ and is usually set at a value below 10 μs.

The temperature to which the transistor $T'_1$ is usually brought is in the vicinity of −120°C in order to minimize its noise level. The optimum value is obtained by regulating the current flowing through the Zener diode $Z_1$ which is placed in the vicinity of the transistor $T'_1$. To this end, the value of the resistor $R_{28}$ is determined experimentally by means of a quadratic voltmeter placed at the output of the amplifier. By way of example in the case of the assembly consisting of cryostat and preamplifier which is employed in the inventors' laboratory, the optimum value of the resistor $R_{28}$ was 62 ohms.

Figure 4:
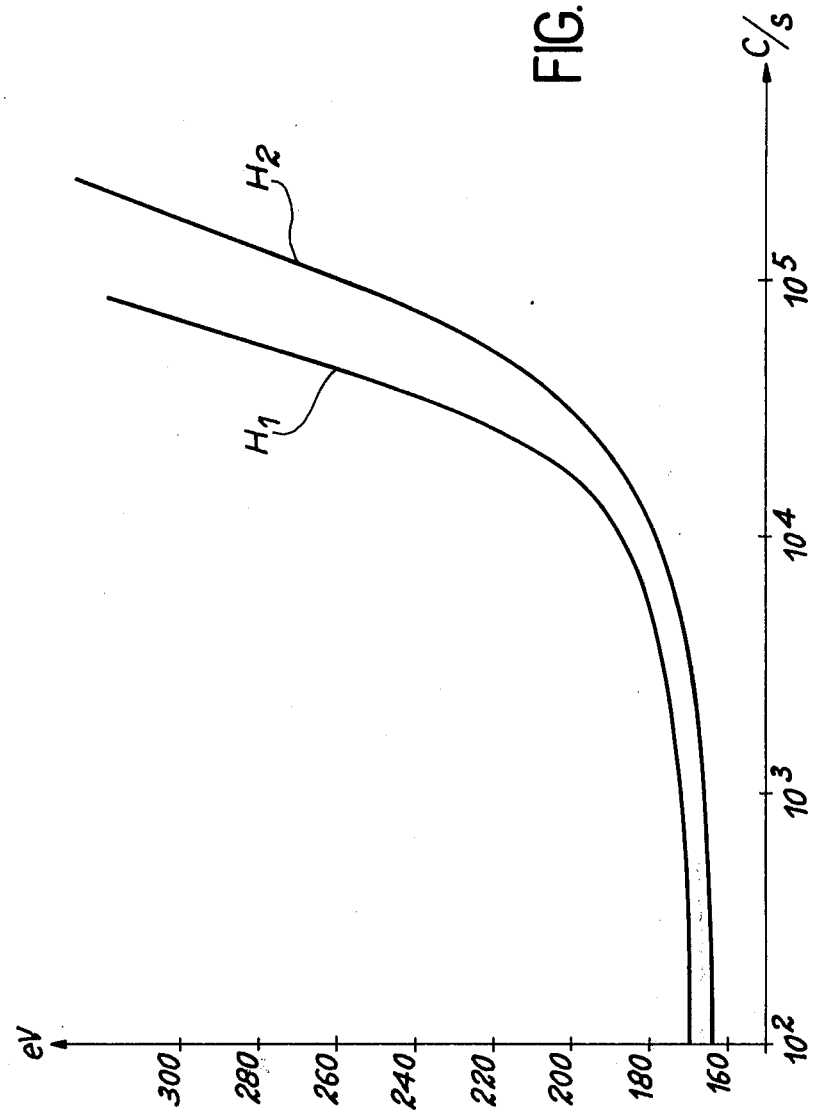
FIG. 4 shows two curves which give the resolution as a function of the count rate in the case of the preamplfier according to the invention and in the case of a preamplifier of known type.

In FIg. 4, the resolution of the preamplifier (expressed in eV) is represented as a function of the count rate (expressed in counts per second on the logarithmic scale) in the case of a Fe-55 source. The curve $H_1$ corresponds to a preamplifier exactly as described above and employed in the prior art. The curve $H_2$ corresponds to the preamplifier in accordance with the invention. This figure shows that in respect of a given resolution, the count rate is approximately twice as high with the preamplifier in accordance with the invention.

The foregoing decription corresponds to the operation of the preamplifier in a pulsed regime. However, the operation of some amplifiers may be disturbed by a preamplifier which operates in a pulsed regime. In that case it is possible to modify the preamplifier to a slight extent so that the transistor $T'_1$ should be continuously illuminated by the electroluminescent diode $D_4$. The modification consists in connecting the base of the transistor $T_7$ to the analog output S of the preamplifier instead of joining it to the output of the gate $M_1$. The base of the transistor $T_8$ is then connected to ground, with the result that the transistors $T_7$ and $T_8$ constitute a Class-A differential stage.

What I claim is:

1. A charge preamplifier essentially comprising an input stage driven by the signal to be amplified, said stage being connected to an amplification stage which is in turn associated with an output stage, and a circuit for applying feedback from the output to the input of said preamplifier, said feedback being of the optoelectronic type, said input stage being such as to comprise a field-effect transistor cooled below ambient temperature, the signal to be amplified being applied to the input gate of said transistor, the load resistance of said transistor being provided by a second field-effect transistor mounted in series with an inductance coil.

2. A preamplifier according to claim 1, wherein the impedance of said inductance coil within the frequency range of the preamplifier is considerably higher than the reciprocal of the slope of the field-effect load transistor.

3. A preamplifier according to claim 1, wherein the drain output of the input transistor is connected on the one hand to the source input of the load transistor through said inductance coil which is mounted in series with a resistor and on the other hand to the input gate of said load transistor.

4. A charge preamplifier essentially comprising an input stage driven by the signal to be amplified, an amplification stage conncted to said input stage, an output stage associated with said amplification stage, and a circuit for applying feedback from the output to the input of said preamplifier, said feedback being of the optoelectronic type, said input stage comprising a first field-effect transistor cooled below ambient temperature, the signal to be amplified being applied to the input gate of said first field-effect transistor, a second field-effect transistor connected in series with an inductance coil as the load resistance of said first field-effect transistor, said feedback circuit comprising a comparator having one input connected to the output of said output stage and the other input connected to a reference voltage source, the output of said comparator being connected to means for initiating the supply of an electroluminescent diode placed opposite to the input of said first field-effect transistor, and a capacitor having one plate connected to the output of said output stage and the other plate connected to the input gate of said first field-effect transistor.

5. A preamplifier according to claim 4, wherein the feedback circuit comprises a delay circuit at the output of the comparator, a bistable circuit controlled by the logical state of the output of the comparator, said circuit being capable of supplying a bipolar transistor whose collector is connected to the input of the electroluminescent diode.

* * * * *